United States Patent
Gempeler et al.

(10) Patent No.: US 10,898,424 B2
(45) Date of Patent: Jan. 26, 2021

(54) PREMIXED BLEND COMPRISING TRIPEPTIDE AND ALGAE EXTRACT

(71) Applicant: DSM IP ASSETS B.V., Heerlen (NL)

(72) Inventors: Mathias Gempeler, Kaiseraugst (CH); Dominik Imfeld, Kaiseraugst (CH); Dirk Weber, Kaiseraugst (CH); Dominique Crestia, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/564,959

(22) PCT Filed: Mar. 21, 2016

(86) PCT No.: PCT/EP2016/056159
§ 371 (c)(1),
(2) Date: Oct. 6, 2017

(87) PCT Pub. No.: WO2016/162198
PCT Pub. Date: Oct. 13, 2016

(65) Prior Publication Data
US 2018/0092823 A1   Apr. 5, 2018

(30) Foreign Application Priority Data

Apr. 8, 2015  (EP) .................................. 15162841

(51) Int. Cl.
| | |
|---|---|
| A61K 8/64 | (2006.01) |
| A61K 8/34 | (2006.01) |
| A61K 8/362 | (2006.01) |
| A61K 8/42 | (2006.01) |
| A61K 8/73 | (2006.01) |
| A61K 8/9722 | (2017.01) |
| A61K 8/96 | (2006.01) |
| A61Q 19/08 | (2006.01) |

(52) U.S. Cl.
CPC ............... *A61K 8/64* (2013.01); *A61K 8/345* (2013.01); *A61K 8/362* (2013.01); *A61K 8/42* (2013.01); *A61K 8/735* (2013.01); *A61K 8/96* (2013.01); *A61K 8/9722* (2017.08); *A61K 2800/805* (2013.01); *A61Q 19/08* (2013.01)

(58) Field of Classification Search
CPC . A61K 8/34; A61K 8/345; A61K 8/36; A61K 8/362; A61K 8/42; A61K 8/64; A61K 8/73; A61K 8/735; A61K 8/97; A61K 8/9706; A61K 8/9722; A61K 8/9728; A61K 36/02; A61K 36/05; A61K 38/06; A61K 2300/00; A61Q 19/00; A61Q 19/08
See application file for complete search history.

(56) References Cited

U.S. PATENT DOCUMENTS

| | | | | |
|---|---|---|---|---|
| 4,699,930 A | * | 10/1987 | Suga ........................ | A61K 8/60 514/25 |
| 6,238,654 B1 | * | 5/2001 | Tournilhac ............... | A61K 8/87 424/401 |
| 6,337,315 B1 | * | 1/2002 | Mahe ....................... | A61K 8/60 424/185.1 |
| 7,700,110 B2 | * | 4/2010 | Zimmerman ........ | A61K 36/899 424/195.15 |
| 7,863,417 B2 | * | 1/2011 | Ziegler .................... | A61K 8/64 530/331 |
| 2006/0193789 A1 | * | 8/2006 | Tamarkin ............... | A61K 8/046 424/47 |
| 2008/0124286 A1 | * | 5/2008 | Lisson ..................... | A61K 8/99 424/61 |
| 2009/0041814 A1 | * | 2/2009 | Nanbu ..................... | A61K 8/73 424/401 |
| 2009/0274770 A1 | * | 11/2009 | Gammelsaeter ....... | A61K 8/987 424/581 |
| 2009/0286749 A1 | * | 11/2009 | Roberto .................. | A61K 8/37 514/23 |
| 2011/0086060 A1 | * | 4/2011 | Bidamant ............ | A61K 31/164 424/195.17 |

FOREIGN PATENT DOCUMENTS

| | | | | |
|---|---|---|---|---|
| CN | 104382833 | | 3/2015 | |
| EP | 1 640 041 | | 3/2006 | |
| EP | 2399648 A2 | * | 12/2011 | ............ A61K 8/673 |
| RO | 126912 | * | 12/2011 | |
| RO | 126 912 | | 4/2014 | |
| WO | WO-2004073666 A1 | * | 9/2004 | ............ A61K 8/375 |
| WO | WO 2009/124971 | | 10/2009 | |

OTHER PUBLICATIONS

Partial English machine translation of Stan Viorel (RO 126912 A0). (Year: 2011).*
English machine translation of Lierhammer (EP 2399648 A2). (Year: 2011).*
English machine translation of Willems et al. (WO 2004073666 A1). (Year: 2004).*
Hannah et al. ("Evaluation of the Biochemical Composition of Four Marine Algae and Its Nutritional Value for Brine Shrimp", IOSR Journal of Pharmacy and Biological Sciences, vol. 6, Issue 3, pp. 47-51). (Year: 2013).*
International Search Report for PCT/EP2016/056159, dated Jun. 20, 2016, 3 pages.
Written Opinion of the ISA for PCT/EP2016/056159, dated Jun. 20, 2016, 6 pages.
Mintel, "Classic Hydrating Night Eye Gelly", *Database GNPD*, Apr. 2012.
Mintel, "Intensive Anti-Aging Cellular Eye Crème", *Database GNPD*, Apr. 2007.

(Continued)

*Primary Examiner* — Matthew R Diaz
(74) *Attorney, Agent, or Firm* — Nixon & Vanderhye P.C.

(57) ABSTRACT

The present invention relates to a blend comprising palmitoyl tripeptide-5, an algae extract, panthenol, water and optionally pullulan and/or sodium hyaluronate.

11 Claims, No Drawings

(56) References Cited

OTHER PUBLICATIONS

Pentapharm: "SYN®—COLL", URL:https://lotioncrafter.com/reference/tech_data_syn_coll.pdf, Aug. 9, 2008.
Pentapharm: "PEPHA®—TIGHT", URL:https://www.lotioncenter.com/pdf/Pepha_Tight.pdf, Apr. 6, 2004.
Pentapharm Service Center Cosmetics, Formulation Guidelines for SYN®-COLL, Version 1, Switzerland, Dec. 16, 2004, pp. 1-9.

* cited by examiner

PREMIXED BLEND COMPRISING TRIPEPTIDE AND ALGAE EXTRACT

This application is the U.S. national phase of International Application No. PCT/EP2016/056159 filed 21 Mar. 2016, which designated the U.S. and claims priority to EP Patent Application No. 15162841.9 filed 8 Apr. 2015, the entire contents of each of which are hereby incorporated by reference.

The present invention relates to a blend comprising palmitoyl tripeptide-5, an algae extract, panthenol, water and optionally pullulan and/or sodium hyaluronate.

Today many consumer goods companies are seeking for premixed blends of cosmetic raw materials with distinct properties in order to facilitate their handling and compounding. Such blends, however, have high requirements in view of their physical properties (e.g. viscosity) as well as their stability such as e.g. the avoidance of significant discoloration upon blending respectively storage as well as crystallization of one or several ingredients contained therein upon storage. Thus, a thorough selection of ingredients as well as suitable concentration ranges have to be found in order to meet these requirements.

Surprisingly, it has been found that a specific premixed blend consisting essentially of palmitoyl tripeptide-5, an algae extract, panthenol, water and either sodium hyaluronate or pullulan fulfills the above mentioned requirements, as they are almost colorless, do not recrystallize upon storage and exhibit a viscosity which allows easy handling in large scale production.

Thus, in a first embodiment the present invention relates to a blend 1 consisting essentially of
(a) 0.05-1 wt.-% of palmitoyl tripeptide-5,
(b) 0.1-10 wt.-% of at least one algae extract,
(c) 5-60 wt.-% of panthenol,
(d) 0-2 wt.-% of sodium hyaluronate,
(e) 0-10 wt.-% of pullulan,
(f) 0-3 wt.-% of at least one preservative,
(g) 0-5 wt.-% of citric acid,
(h) 0-5 wt.-% of ethylhexylglycerin, and
(i) at least 20 wt.-% of water.

In a preferred embodiment the blend 1 is a blend 2 consisting essentially of
(a) 0.05-1 wt.-% of palmitoyl tripeptide-5,
(b) 0.5-7 wt.-% of at least one algae extract,
(c) 10-55 wt.-% of panthenol,
(d) 0-1 wt.-% of sodium hyaluronate,
(e) 0-10 wt.-% of pullulan,
(f) 0-2 wt.-% of at least one preservative,
(g) 0-3 wt.-% of citric acid,
(h) 0-3 wt.-% of ethylhexylglycerin, and
(i) at least 20 wt.-% of water.

In an even more preferred embodiment the blend 1 is a blend 3 consisting essentially of
(a) 0.05-1 wt.-% of palmitoyl tripeptide-5,
(b) 0.5-7 wt.-% of at least one algae extract,
(c) 15-50 wt.-% of panthenol,
(d) 0.1-1 wt.-% of sodium hyaluronate,
(e) 0.1-2 wt.-% of at least one preservative,
(f) 0.1-1 wt.-% of citric acid,
(g) 0.1-1 wt.-% of ethylhexylglycerin and
(h) at least 20 wt.-% of water.

In another preferred embodiment the blend 1 is a blend 4 consisting essentially of
(a) 0.1-1 wt.-% of palmitoyl tripeptide-5
(b) 1-5 wt.-% of at least one algae extract,
(c) 25-50 wt.-% of panthenol,
(d) 0.1-1 wt.-% of sodium hyaluronate,
(e) 0.1-2 wt.-% of at least one preservative,
(f) 0.1-1 wt.-% of citric acid,
(g) 0.1-1 wt.-% of ethylhexylglycerin, and
(h) at least 20 wt.-% of water.

In another advantageous embodiment the blend 1 is a blend 5 consisting essentially of
(a) 0.1-5 wt.-% of palmitoyl tripeptide-5
(b) 1-3 wt.-% of at least one algae extract,
(c) 25-40 wt.-% of panthenol,
(d) 0.1-1 wt.-% of sodium hyaluronate,
(e) 0.1-2 wt.-% of at least one preservative,
(f) 0.1-1 wt.-% of citric acid,
(g) 0.1-1 wt.-% of ethylhexylglycerin, and
(h) at least 20 wt.-% of water.

In another preferred embodiment the blend 1 is a blend 6 consisting essentially of
(a) 0.05-1 wt.-% of palmitoyl tripeptide-5
(b) 0.5-7 wt.-% of at least one algae extract,
(c) 5-15 wt.-% of panthenol,
(d) 2.5-10 wt.-% of pullulan,
(e) 0.1-2 wt.-% of at least one preservative,
(f) 0.1-1 wt.-% of citric acid,
(g) 0-1 wt.-% of ethylhexylglycerin, and
(h) at least 45 wt.-% of water.

In another preferred embodiment the blend 1 is a blend 7 consisting essentially of
(a) 0.1-0.5 wt.-% of palmitoyl tripeptide-5
(b) 1-3 wt.-% of at least one algae extract,
(c) 7-13 wt.-% of panthenol,
(d) 3-8 wt.-% of pullulan,
(e) 0.1-2 wt.-% of at least one preservative,
(f) 0.1-1 wt.-% of citric acid, and
(g) 0.1-1 wt.-% of ethylhexylglycerin, and
(h) at least 45-wt.-% of water.

The term 'the blend consists essentially of' as used according to the present invention means that the total amount of the listed ingredients ideally sum up to 100 wt.-%. It is however not excluded that small amounts of impurities or additives may be present, with the proviso that the total amount of such impurities or additives is preferably less than 3 wt.-%, more preferably less than 2 wt.-%, most preferably less than 1 wt.-% and which are introduced via the respective raw materials (a)-(h).

It is furthermore well understood, that the (total) amount of water in the blend is the sum of water added via the respective raw materials such as e.g. via an aqueous algae extract and 'free' water which is used to adjust the blend to 100 wt.-%)

Preferably the palmitoyl tripeptide-5 (a) is dissolved in this 'free' water before blending with the other ingredients.

The blends according to the present invention are colourless to yellowish liquids and exhibit a viscosity in the range of less than 3000 mPas, preferably less than 2000 mPAS, most preferably less than 1500 mPas (measured with Brookfield RVDV-II+, spindle 3 at 25° C. with a shear rate of 10 rpm for 30 s). The pH of the blends according to the present invention is adjusted such that the respective blend exhibits a pH value of approximately 4.0-6.0, preferably 4.5-5.5. The pH is adjusted with the citric acid after preparation of the blend, but before filtration.

Palmitoyl tripeptide-5 [CAS-Nr. 501-36-0], is a tripeptide which is esterified with palmitic acid having the sequence Palm-Lys-Val-Lys-OH (Pal-KVK). Palmitoyl tripeptide-5 and can be prepared according to standard methods in the art such as e.g. outlined in WO2004099237. It can be used as such or in the form of its salts such as preferably as trifluoroacetate salt (Palm-Lys-Val-Lys-OH*2 TFA).

The algae extract is preferably an extract of the biotechnologically produced microalgae *Duniella salina* or the microalgae *Nannochloropsis oculata* as well as mixtures thereof. Such extracts are obtainable by cultivation of the respective algae, followed by harvesting the cells. Afterwards the harvested cells are rehydrated and extracted with hot water. The crude extract is subsequently centrifuged and ultrafiltrated. In the preparation of the blend, the algae extract can be used in dried form or in the form of a concentrated aqueous algae extract with a known solid content. Preferably, the algae extract is added to the blend in the form of a concentrated aqueous algae extract, having a known algae extract content (solid content). Preferably an aqueous algae extract having an algae extract content selected in the range of 0.5 to 10 wt.-%, preferably in the range of 1 to 5 wt.-%, based on the total aqueous algae extract, is used in the preparation of the blends according to the present invention.

In a particular advantageous embodiment blend 1 to 5 contain only one algae extract which is derived from *Duniella salina*—in the absence of any further algae extract. In another particular advantageous embodiment blend 1, 2, 6 and 7 contain a mixture of algae extracts which are derived from *Duniella salina* and *Nannochloropsis oculata*—in the absence of any further algae extract. If a *Duniella salina* and a *Nannochloropsis oculata* algae extract is present, then preferably the ratio (by weight) of the *Duniella salina* to the *Nannochloropsis oculata* algae extract is selected in the range of 0.5:1 to 1 to 0.5, such as preferably in the range of 0.8:1 to 1:0.8.

Panthenol [CAS 81-13-0] is e.g. commercially available as D-panthenol or D-panthenol 75L at DSM Nutritional Products Ltd.

The term sodium hyaluronate [CAS 9067-32-7] as used herein refers to the sodium salt of hyaluronic acid. Preferably low molecular weight sodium hyaluronate is used in the blends according to the present invention such as sodium hyaluronate having a molecular weight (MW) in the range of 10 to 800 kDa, preferably having a MW in the range of 200 to 600 kDa and most preferably having a MW in the range of 350 to 550 kDa. Such sodium hyaluronate is e.g. available under the tradename Hyaluronic acid BT LMW 350'-550' at DSM Nutritional products Ltd as well as BasHyal (MW 100-300 kDa) or Renovhyal (MW 15-50 kDa) at Soliance.

Pullulan is a polysaccharide produced by the yeast like fungus *Aureobasidium pullulans*. Pullulan is an essentially linear glucan consisting mainly of 1,6-linked maltotriose and some interspersed maltotetraose units. Pullulan is e.g. commercially available as Aqua beta (from Daiso, Co., Ltd.) or Pullulan (from Hayashibara Co., Ltd.).

The blend preferably comprises at least one cosmetically acceptable preservative. More preferably the at least one cosmetically acceptable preservative is selected from the group consisting of phenoxyethanol, sodium benzoate and potassium sorbate as well as mixtures thereof. Most preferably phenoxyethanol, sodium benzoate and potassium sorbate are present in the blend according to the present invention, advantageously in the absence of any further preservatives.

The blends according to the present invention can be prepared by a person skilled by conventional blending processes such as batch processing which includes a shear mixing of the ingredients, usually with a high shear turbine or rotor-stator device and a high flow, low shear mixing device.

Thus, in another embodiment, the invention relates to a process of preparing a blend according to the present invention, said method comprising the steps of
a. Dissolving palmitoyl-tripeptide-5 (a) in water,
b. Adding the ingredients (b) to (h), respectively (i) to the obtained solution,
c. Mixing the ingredients to form a blend,
d. Filtering the resulting blend, and
e. Filling the resulting blend into containers.

In a particular preferred embodiment, the blend is prepared by dissolving palmitoyl tripeptide-5 in water, followed by the addition of panthenol, sodium hyaluronate and the at least one algae extract. Then the obtained blend is thoroughly mixed, followed by the addition of the at least one preservative and ethylhexylglycerin. The final blend is then pH adjusted with citric acid, filtered and filled into containers.

The following examples are provided to further illustrate the compositions and effects of the present invention. These examples are illustrative only and are not intended to limit the scope of the invention in any way.

Blends

The blends were prepared by conventional mixing of the ingredients outlined in table 1 with a rotor-stator mixer. The thus obtained blends are clear, slightly yellow liquids which are stable upon storage for 3 month at 8° C. without the occurrence of any crystallization or discoloration.

TABLE 1

| Blends | | |
|---|---|---|
| Name | Blend 1 [Wt.-%] | Blend 2 [Wt.-%] |
| Pal-Lys-Val-Lys-OH *2TFA | 0.2 | 0.25 |
| Water | Ad 100 | Ad 100 |
| D-Panthenol | 30.0 | 10.0 |
| *Dunaliella Salina* Extract | 1.2 | 0.65 |
| *Nannochloropsis oculata* Extract | | 0.6 |
| Sodium hyaluronate (MW 350-550 kDa) | 0.4 | |
| Pullulan | | 5.0 |
| Sodium Benzoate | 0.2 | 0.3 |
| Potassium Sorbate | 0.05 | 0.05 |
| Phenoxyethanol | 1.5 | 1.0 |
| Citric acid | 0.5 | 0.5 |
| Ethylhexylglycerin | 0.13 | 0.2 |
| pH | 5.3-5.5 | 4.9-5.1 |
| Viscosity (Brookfield, RVDV-II+, spindle 3) Measured at 25° C. with shear rate of 10 rpm for 30 s | <1500 mPas | <1000 mPas |

The invention claimed is:

1. A blend consisting of:
(a) 0.05-1 wt. % of palmitoyl tripeptide-5,
(b) 0.5-7 wt. % of at least one algae extract selected from the group consisting of an extract of microalgae *Duniella salina* and an extract of microalgae *Nannochloropsis oculata*,
(c) 15-50 wt. % of panthenol,
(d) 0.1-1 wt. % of sodium hyaluronate,
(e) 0.1-2 wt. % of at least one preservative,
(f) 0-1 wt. % of citric acid,
(g) 0.1-1 wt. % of ethylhexylglycerin and
(h) at least 20 wt. % of water.

2. A blend consisting of:
(a) 0.05-1 wt. % of palmitoyl tripeptide-5,
(b) 0.5-7 wt. % of at least one algae extract selected from the group consisting of an extract of microalgae *Duniella salina* and an extract of microalgae *Nannochloropsis oculata*, (c) 5-15 wt. % of panthenol,
(d) 2.5-10 wt. % of pullulan,
(e) 0.1-2 wt. % of at least one preservative,
(f) 0-1 wt. % of citric acid,
(g) 0-1 wt. % of ethylhexylglycerin, and
(h) at least 45 wt. % of water.

3. The blend according to claim 1 or 2, wherein the algae extract in the blend consists of only the extract of the microalgae *Duniella salina*.

4. The blend according to claim 1 or 2, wherein the algae consists of both an extract of the microalgae *Duniella salina* and an extract of the microalgae *Nannochloropsis oculata*.

5. The blend according to claim 1 or 2, wherein the at least one preservative is selected from the group consisting of phenoxyethanol, sodium benzoate, potassium sorbate and mixtures thereof.

6. The blend according to claim 1 or 2, wherein the blend is a liquid having a pH value of about 4.0-6.0 and a viscosity in the range of less than 3000 mPa·s.

7. The blend according to claim 6, wherein the pH value of the blend is about 4.5-5.5 and the viscosity of the blend is less than 2000 m Pas.

8. A process for preparing the blend according to claim 1 or 2, wherein the process comprises the steps of:
   (i) dissolving the palmitoyl tripeptide-5 in water to obtain an aqueous solution of palmitoyl tripeptide-5,
   (ii) adding all remaining ingredients to the aqueous solution of palmitoyl tripeptide-5 obtained according to step (i),
   (iii) mixing the ingredients into the aqueous solution of palmitoyl tripeptide-5 to form a blend thereof,
   (iv) filtering the blend, and
   (v) filling the filtered blend into containers.

9. A process for preparing the blend according to claim 1, wherein the process comprises the steps of:
   dissolving the palmitoyl tripeptide-5 in water to obtain an aqueous solution of palmitoyl tripeptide-5,
   (ii) adding the panthenol, the sodium hyaluronate and the at least one algae extract to the aqueous solution of palmitoyl tripeptide-5 obtained according to step (i),
   (iii) mixing the panthenol, the sodium hyaluronate and the at least one algae extract into the aqueous solution of palmitoyl tripeptide-5 to form a blend thereof,
   (iv) adding the at least one preservative and the ethylhexylglycerin to the blend,
   (v) adding citric acid to the blend in an amount sufficient to adjust pH of the blend to a value of 4.0-6,
   (vi) filtering the blend, and
   (vii) filling the filtered blend into containers.

10. The process according to claim 8, wherein step (iii) is performed by mixing with a mixing device.

11. The process according to claim 10 wherein the mixing device is a shear turbine or a rotor-stator mixing device.

* * * * *